(12) United States Patent
Barbeau (10) Patent No.: US 7,773,971 B1
(45) Date of Patent: Aug. 10, 2010

(54) WIRELESS SERVICE INCENTIVE SYSTEM FOR PROMOTING PHYSICAL HEALTH

(75) Inventor: Pierre Barbeau, Leawood, KS (US)

(73) Assignee: Sprint Spectrum L.P., Overland Park, KS (US)

( * ) Notice: Subject to any disclaimer, the term of this patent is extended or adjusted under 35 U.S.C. 154(b) by 793 days.

(21) Appl. No.: 11/613,567

(22) Filed: Dec. 20, 2006

(51) Int. Cl.
*H04M 11/00* (2006.01)
*G06Q 30/00* (2006.01)

(52) U.S. Cl. .................. 455/406; 705/14.1

(58) Field of Classification Search ........... 455/406, 455/404.1; 705/14.1; 379/111–134
See application file for complete search history.

(56) References Cited

U.S. PATENT DOCUMENTS

| | | | |
|---|---|---|---|
| 5,920,847 A | * | 7/1999 | Kolling et al. ............ 705/40 |
| 6,807,409 B1 | * | 10/2004 | Davidson et al. ............ 455/406 |
| 2002/0013717 A1 | * | 1/2002 | Ando et al. ............ 705/4 |
| 2003/0013434 A1 | * | 1/2003 | Rosenberg et al. ............ 455/414 |
| 2003/0065561 A1 | | 4/2003 | Brown et al. |
| 2006/0111944 A1 | | 5/2006 | Sirmans, Jr. et al. |

OTHER PUBLICATIONS

Abstract of Japanese Publication No. JP2005038366, published Feb. 10, 2005.
Abstract of Japanese Publication No. JP2002176426, published Jun. 21, 2002.

* cited by examiner

*Primary Examiner*—George Eng
*Assistant Examiner*—Chayce Bibbee (57) ABSTRACT

A wireless communication device, such as a cell phone, will transmit into a network an indication of a person's health status, such as a quantity of exercise in which the person engaged or a measure of some aspect of the person's body systems, as determined by a health status sensor provided separate from or integral with the wireless communication device. Based on the reported health status information, the network will then register a discount on the price that a wireless service provider charges for providing the wireless communication device with wireless communication service.

22 Claims, 4 Drawing Sheets

WIRELESS SERVICE INCENTIVE SYSTEM FOR PROMOTING PHYSICAL HEALTH

FIELD OF THE INVENTION

The present invention relates to telecommunications and, more particularly, to associating wireless telecommunication service with physical health.

BACKGROUND

The art and popularity of wireless communications has grown significantly over recent years. Further, at the same time, society has seen an increased focus on the desire to maintain healthy lifestyles. Given that many people have become accustomed to carrying a cell phone or other wireless communication device, it would be advantageous to use such a device as an incentive to maintain healthy living.

SUMMARY

The present invention provides for associating wireless telecommunication service with physical health. As a general matter, a person will have a wireless communication device that engages in wireless communication service provided by a wireless service provider, and the wireless service provider will charge a price for providing the service. Incorporated into the wireless communication device, or communicatively linked with the wireless communication device, will then be a health status sensor, which will function to measure any of a variety of physical health characteristics of the person—such as an amount of exercise in which the user is engaging, or a particular state of the person's body such as the person's heart rate, blood pressure, blood sugar level, cholesterol level, or the like.

In accordance with the invention, the wireless communication device will then transmit to a network server an indication of the measured health characteristic, and, based on at least that reported health characteristic, a network entity will then register a discount on the price that the wireless service provider charges for providing the wireless communication device with wireless communication service. For instance, the wireless service provider may reduce the price that it charges for providing the wireless communication service, or the wireless service provider may issue a credit to the subscriber, thus effectively reducing the net price.

In an exemplary embodiment, for instance, a network entity may determine that the reported health characteristic meets a predefined threshold—such as a threshold quantity of exercise or a threshold body characteristic. If the reported health characteristic meets the predefined threshold, then the price that the wireless service provider charges for the wireless communication device to engage in wireless communication service may be discounted. Alternatively, a network entity may determine that a cumulative total or other measure of the reported health characteristic and other reported health characteristics (e.g., the average or total reported quantity of exercise over time, or an average body system characteristic over time) meets a defined threshold. And if that measure of the reported health characteristic meets the predefined threshold, then the price that the wireless service provider charges for the wireless communication device to engage in wireless communication service may be discounted.

In this regard, various levels of thresholds and price discounts can be provided. For instance, if the person engages in a first threshold level of exercise, then the price charged for the wireless communication device to engage in wireless communication service may be discounted by a first amount, and if the person engages in a second, higher threshold level of exercise, then the price charged for the wireless communication device to engage in wireless communication service may be discounted by a second, greater amount. Similar examples are possible with respect to body system characteristics, such as heart rate, blood pressure, blood sugar level, cholesterol level, or the like.

Aspects of the invention may thus be carried out by equipment carried by or otherwise associated with the end-user, such as the wireless communication device and (perhaps integrated) health status sensor, with the health status sensor measuring the person's physical health characteristic, and the wireless communication device reporting the measured health characteristic to the network server. Other aspects of the invention may be carried out by equipment in the network, such as the network server and (perhaps integrated) wireless service provider's account or billing system, with the network server receiving the person's reported health characteristic, and with the wireless service provider's account or billing system registering a price discount based at least in part on the reported health characteristic.

Optimally, the threshold health characteristic of the person will constitute a desirable health characteristic, such as a desirable quantity of exercise, a desirable heart rate, a desirable blood pressure level, a desirable blood sugar level, a desirable cholesterol level, or the like. Further optimally (but not necessarily), the person whose health characteristic is being measured is the person responsible for paying the wireless service fee. Accordingly, by providing a wireless service discount as a reward for the person achieving the desirable health status, the invention functions to promote achievement of the desirable health status, and therefore the invention functions to promote healthy living.

These as well as other aspects, advantages and alternatives will become more apparent to those of ordinary skill in the art by reading the following detailed description, with reference where appropriate to the accompanying drawings.

DETAILED DESCRIPTION

1. Overview

In one respect, an exemplary embodiment of the invention may take the form of a method for associating wireless communication service with physical health. According to the exemplary method, a network server would receive a message transmitted to the network server from a wireless communication device carried by a person, and the message would contain data indicating at least one health characteristic of the person. The exemplary method would then involve granting a discount on a price that the wireless service provider charges for providing wireless communication service for the wireless communication device.

In particular, a network entity may determine that the at least one reported health characteristic meets a threshold, and the act of granting the discount based on the at least one reported health characteristic may then involve granting the discount in response to determining that the at least one reported health characteristic meets the threshold. Furthermore, the act of determining that the at least one reported health characteristic meets the threshold may involve receiving multiple health characteristic reports (at once, or separately communicated from the wireless communication device), establishing a measure based (e.g., average, total, or other measure) based on the multiple health characteristic reports, and determining that the measure meets the threshold.

The act of granting the discount on the price that the wireless service provider charges for use of the wireless communication device to engage in wireless communication service may involve reducing the price. For instance, if the person or other entity pays a monthly recurring charge or per-unit charge for wireless service, the act of granting the discount may involve changing the applicable service account record to lower the monthly recurring charge or per-unit charge. Alternatively, the act of granting the discount on the price that the wireless service provider charges for use of the wireless communication device to engage in wireless communication service can involve applying a credit to a service account for the wireless communication device, to thereby effectively reduce the price. Other mechanisms for granting the discount may be possible as well.

In the exemplary method, each health characteristic of the person may take various forms but generally relates in some manner to the physical health of the person. By way of example, the health characteristic may comprise a quantity of exercise in which the person has engaged, and so the threshold may comprise a threshold quantity of exercise. For instance, the quantity of exercise may comprise a count of steps determined to have been taken by the person, so the threshold may comprise a threshold number of steps. In this regard, the wireless communication device carried by the person could itself contain a pedometer, and the pedometer (and thus the wireless communication device) could determine the count of steps taken by the person when the person is in motion (e.g., walking or running). Alternatively, the person may carry a pedometer separate from the wireless communication device, and the wireless communication device can receive from the pedometer, via a personal area network (e.g, Wi-Fi, BLUETOOTH, or cable connection) an indication of the count of steps taken by the person.

As another example, the health characteristic may comprise any health status that is established by a body sensor applied in any manner to the person and reported from the body sensor to the wireless communication device. A pedometer is one example of this arrangement, with the health characteristic comprising a number of steps taken by the person. Other examples include (i) a cholesterol sensor, with the health characteristic comprising a cholesterol level of the person as measured by the sensor, (ii) a blood pressure sensor, with the health characteristic comprising a blood pressure of the person as measured by the sensor, (iii) a heart rate monitor, with the health characteristic comprising a heart rate of the person as measured by the sensor, and (iv) a body temperature sensor, with the health characteristic comprising a temperature of the person's body.

These or other sensors may be carried by, implanted in, or otherwise associated with the person and regularly applied to the person (through any of various means now known or later developed) in order to passively monitor the person's health status or may be actively applied to the person (e.g., by manual application and/or invocation) to determine the person's health characteristic. For instance, a blood sugar sensor could be applied to the person's fingertip to measure the person's blood sugar level, and the measured blood sugar level may then be conveyed through a personal area network (e.g., connector, cable, or wireless connection, directly or indirectly), from the blood sugar sensor to the wireless communication device, for transmission of an indication of the blood sugar level in turn from the wireless communication device to the network server.

As another example, a heart rate monitor implanted in the person could report the person's heart rate over a personal area network to the wireless communication device, for transmission of an indication of the heart rate in turn from the wireless communication device to the network server. Numerous other examples are possible as well, within the scope of the invention. Further, a body sensor could just as well be integrated with the wireless communication device as an integral unit.

Furthermore, the wireless communication device carried by the person can take various forms. In one embodiment, for instance, the device can be a cell phone or wirelessly-equipped personal digital assistant (PDA) of the type that is capable of engaging in wireless packet data communication, so as to facilitate sending of health status data to the network server. In another embodiment, the device could be a more specialized device that is arranged specifically to send health status data to the network server and might possibly have one or more integrated health status sensors, regardless of whether such a device also functions as a cell phone or for wireless communication purposes other than conveying health status data to the network server.

In another respect, an exemplary embodiment of the invention may take the form of a system comprising (i) a portable wireless communication device usable by a person to engage in wireless communication service via a radio access network, wherein a wireless service provider charges a prices for providing wireless communication service for the portable wireless communication device, and (ii) a network server communicatively accessible by the portable wireless communication device (e.g., able to receive communications transmitted from the portable wireless communication device) via the radio access network.

In accordance with this embodiment, the portable wireless communication device would include device logic that is executable by a processor to report at least one health characteristic of the person via the radio access network to the network server. Further, the network server would include server logic that is executable by a processor, based on the at least one reported health characteristic, to grant a discount on the price that the wireless service provider charges for providing wireless communication service for the portable wireless communication device.

The server logic may, for instance, determine that the at least one reported health characteristic meets a threshold, and the server logic may grant the discount on the price in response to determining that the at least one reported health characteristic meets the threshold. Further, the server logic may receive multiple reported health characteristics from the portable wireless communication device, may establish a measure based on the multiple reported health characteristics, and may grant the discount in response to determining that the measure meets the threshold.

In the exemplary system, the logic may grant the reduction in price by causing a signal to be sent to the wireless service provider directing the wireless service provider to apply a price reduction. The wireless service provider may then receive the signal and responsively apply the price reduction to the service account associated with the portable wireless communication device. If the network server is part of the wireless service provider's network, the signal can still be sent "to" the wireless service provider if it the signal is sent to any entity of the wireless service provider, such as to the wireless service provider's billing or account-records system for instance. Application of the price reduction may then involve other functions, such as notating or modifying the service account record for the wireless communication device, to effect the price reduction.

Furthermore, the various aspects discussed above with respect to the exemplary method can be applied equally to the exemplary system. For instance, the health status sensor can be incorporated in the portable wireless communication device or can be provided and applied separately to enable the portable wireless communication device to determine the person's health characteristic. And the sensor can take various forms, measuring various types of health information. Additionally, the portable wireless communication device can take various forms, such as a cell phone or other wirelessly-equipped device, whether or not dedicated to the function of reporting health characteristics to the network server.

2. Example Architecture

Figure 1:
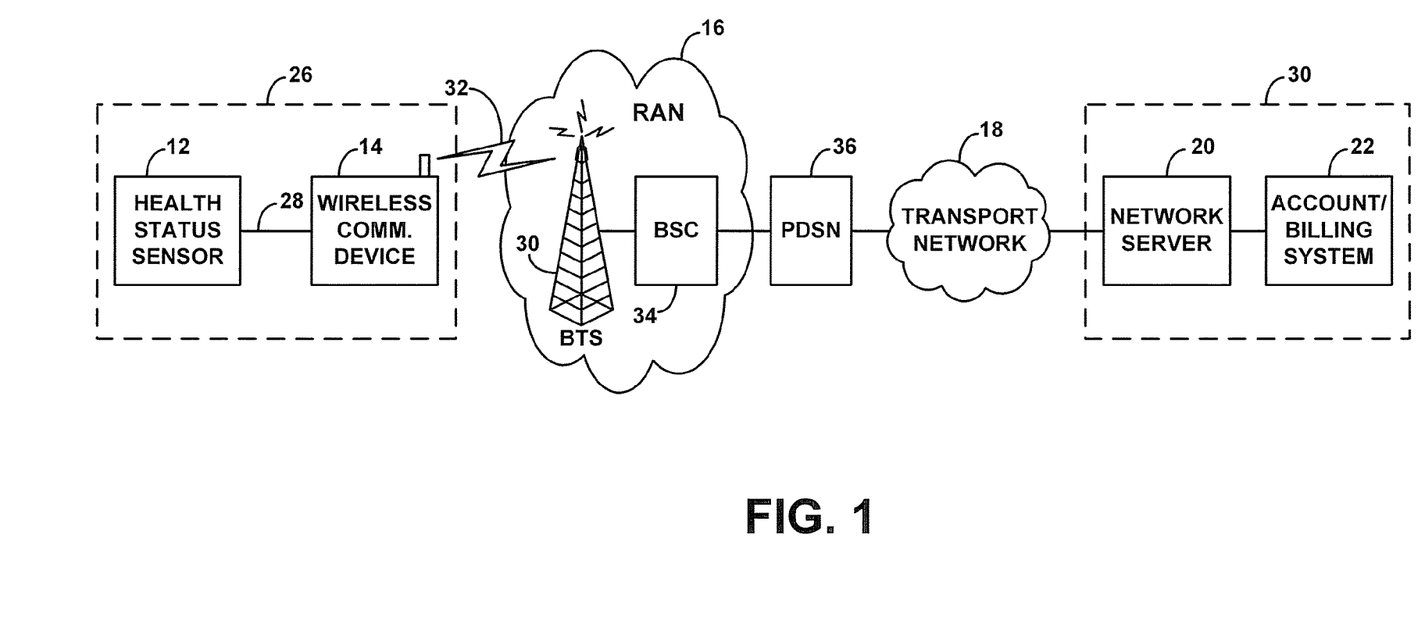
FIG. 1 is a simplified block diagram of a system arranged to operate in accordance with an exemplary embodiment of the invention.

Referring now to the drawings, FIG. 1 is a simplified block diagram depicting a system arranged to operate in accordance with the exemplary embodiment. It should be understood, however, that this and other arrangements and descriptions provided throughout this document are intended to be examples only and are not intended to be limiting. Thus, various elements and/or functions can be combined, distributed, eliminated, re-ordered, or otherwise modified from the arrangements shown and described. Further, various functions described herein as being carried out by one or more entities could be readily carried out by software, firmware, and/or hardware.

As shown in FIG. 1, the exemplary system includes, from left to right, a health status sensor 12, a portable wireless communication device 14, a radio access network 16, a transport network 18, a network server 20, and a wireless service provider's account/billing system 22.

As a general matter, in this arrangement, the health status sensor 12 functions to measure a physical health characteristic of a person, and the portable wireless communication device 14 functions to transmit an indication of the measured health characteristic via the radio access network 16 and transport network 18 to the network server 20. In turn, the network server 20 and/or the wireless service provider's account/billing system 22 or other network equipment then functions to determine if the reported health status meets a designated threshold and, if so, to discount the price that the wireless service provider charges for providing the wireless communication device 14 with wireless communication service.

In practice, health status sensor 12 comprises a mechanism for sensing, measuring, or otherwise determining one or more health-related characteristics a person. Health status sensor 12 is thus arranged to be applied to, on, in, about, or otherwise with respect to the person so as to determine the person's health characteristic. For instance, the health status sensor could be worn by the person, attached to the person, carried by the person, implanted in the person, held upon the person, or otherwise applied to the person, the specific application and means of use depending on the type of sensor and the type of health status information being determined, among possibly on other factors.

Suitable health status sensors for sensing various types of health related characteristics are well known in the art and are therefore not described here in detail. As noted above, for instance, examples include a pedometer for determining the number of steps taken by the person, a blood pressure sensor for determining the person's blood pressure, a heart rate sensor for determining the person's heart rate, a blood sugar sensor for determining the person's blood sugar, a cholesterol sensor for determining the person's cholesterol level, and a temperature sensor for determining the person's body temperature. Numerous other examples exist now as well or will be developed in the future, and any such sensors can be used in accordance with the invention to measure the person's health status. Further, it should be understood that the accuracy of the determination that the health status sensor makes regarding the person's health characteristic is not critical, although the health status sensor is preferably accurate.

In accordance with the exemplary embodiment, health status sensor 12 is arranged to produce an output signal indicating the determined health status and is further arranged to convey that output signal, or some other indication of the determination, to the wireless communication device 14 for transmission in turn to the network server 14. For instance, if the health status sensor 12 is a pedometer, the health status sensor may generate an output signal indicating a number of steps taken by the person. In conventional pedometers, such an output might be presented on a display screen of the pedometer, for viewing by the person. In the exemplary embodiment, such an output, or an associated indication, may instead or additionally be transmitted to the wireless communication device. The same is the case for other sorts of health status sensors, and thus for other types of health characteristics.

Wireless communication device 14, in turn, is an apparatus arranged to engage in wireless communication via radio access network 16 and, further, to communicate via radio access network 16 with one or more entities on transport network 18, such as network server 20 for instance. As such, wireless communication device 14 may be a cell phone, a wirelessly-equipped PDA, or another sort of device equipped to engage in wireless packet data communication according to any of a variety of wireless communication protocols now known or later developed, such as any of the well known CDMA, TDMA, GSM, 802.11, BLUETOOTH, or WiMax protocols for instance.

Wireless communication device 14 is preferably a portable wireless communication device suitable for being carried by the person, in a pocket, in a single hand, or the like. In operation, the wireless communication device 14 may be carried by the person whose health status is measured. Thus, the person may physically possess the wireless communication device, regardless of whether the person is actually moving at the time, and regardless of how the person possesses the device. Alternatively, the wireless communication device could be operated by the person without being physically possessed or carried by the person. For instance, the wireless communication device could be provided in a fixed docking station or the like and operated from that position. Furthermore, while it is preferred that the wireless communication device be a handheld portable device, other sorts of wireless communication devices could be used instead.

In accordance with the exemplary embodiment, wireless communication device 14 is arranged to determine the health characteristic of the person and preferably does so by receiving an indication of the person's health characteristic from health status monitor 12. Wireless communication device 14 is then arranged to report the determined health characteristic to network server 20, to facilitate registration of a discount on the price that the wireless service provider charges for providing the wireless communication device 14 with wireless communication service. As a general matter, wireless communication device 14 can be programmed with instructions executable by a processor to carry out the functions of determining and reporting the person's health characteristic.

As illustrated by the dashed box 26 surrounding the health status sensor 12 and wireless communication device 14 in FIG. 1, it is possible that the health status sensor 12 and wireless communication device 14 could be integrated together in the form of an integral unit or system, such as a unit having a housing and containing both the function of the health status sensor 12 and the function of the wireless communication device 14. Such an integrated unit could further include various accessories, such as externally coupled sensing mechanisms and externally coupled wireless communication antennas or user interfaces for instance.

The combination 26 of health status sensor 12 and wireless communication device 14 could be provided as a specialized device, sold or otherwise distributed by the wireless service provider, by a health service provider, or by some other entity, possibly in combination with a service subscription package that enables the combined unit to report determined health status information to the network and that costs less depending on the health achievements of the person. For instance, the service subscription package may have a monthly fee, with the fee decreasing if the reported health information indicates that the person is engaging in a threshold extent of exercise.

In a preferred embodiment, such a combined unit 26 will also provide the person with more robust and diverse wireless communication service, such as general telephony or personal information management (PIM) service (e.g., e-mail messaging service, calendar management service, contact management service, etc.) for instance, so that the person can benefit from using the device to engage in assorted useful wireless communications. Yet in accordance with the exemplary embodiment, the person (or other entity who pays the price that the wireless service provider charges for the wireless communication service) would also benefit from a discounted wireless service price in response to the person's health status reaching a threshold level.

Depending on perspective, the combined unit 26 may take the form of a wireless communication device 14 having integrated health status monitoring and reporting functionality (with an integrated health status sensor module), or the combined unit 26 may take the form of a health status sensor 12 having integrated wireless communication and health status reporting functionality (with an integrated wireless communication module).

Alternatively, the health status sensor 12 could be provided separately from the wireless communication device 14, and the two could be arranged to communicate with each other, so that the health status sensor 12 could report determined health characteristic information to the wireless communication device 14, and so that the wireless communication device 14 could determine the person's health characteristic by receiving an indication of the person's health characteristic as determined by the health status sensor 12. In this arrangement, the health status sensor 12 could just as well take any of the forms noted above, and the wireless communication device 14 could equally take any of the forms noted above, again preferably providing the person with wireless communication service as a general matter.

If the health status sensor 12 and wireless communication device 14 are provided as separate pieces, some mechanism should be provided to facilitate communication of the person's health characteristic information from the health status sensor 12 to the wireless communication device 14. For this purpose, a communication link 28 could be provided between the health status sensor 12 and the wireless communication device 14.

Communication link 28 may comprise a short-range wireless link, such as an 802.11 or BLUETOOTH link, for instance, in which case the health status sensor 12 and the wireless communication device 14 would each include, be connected with, or otherwise be served by a respective short-range wireless transceiver set to communicate with the transceiver in the other. Those skilled in the art could readily incorporate a BLUETOOTH transceiver into a small health status sensor, for instance, just as BLUETOOTH transceivers are commonly integrated into small cell phone ear-buds and other equipment today.

Alternatively, the communication link could be a direct cable and/or connector link between the health status sensor 12 and the wireless communication device 14. For instance, a USB or other cable could extend from a port on the sensor 12 to a port on the device 14, or either the sensor or device could have a flip-out USB or other connector that plugs into a corresponding port on the other.

Numerous other arrangements for communicatively linking the health status sensor 12 with the wireless communication device 14 are possible as well. Further, it should be understood that the link between the health status sensor 12 and the wireless communication device 14 may or may not be in place at the time the health status sensor 12 functions to determine the person's health characteristic. In practice, if the communication link 28 exists at the time the health characteristic is determined, the health status sensor 12 could report the determined characteristic to the wireless communication device at that time (or later if desired). Alternatively, if the link 28 does not exist at that time, then after the health status sensor 12 determines the person's health characteristic, the person or some other entity could communicatively link together the health status sensor 12 and the wireless communication device and invoke a function on either or both devices to cause the determined health characteristic to be communicated from the health status sensor 12 to the wireless communication device 14.

Radio access network 16 is preferably operated by the wireless service provider that provides the wireless communication device 14 with wireless communication service, such as a cellular wireless carrier for instance. In particular, the act of providing the wireless communication device 14 with wireless communication service may involve allowing the wireless communication device to engage in communication with or via the radio access network 16. For instance, the act may involve allowing the wireless communication device to engage in legacy telephone communications via the radio access network and/or data communications (such as voice-over-IP communications or wireless web browsing) via the radio access network 16.

The radio access network 16 may take various forms, depending on factors such as the type of wireless communication in which the wireless communication device will engage. As illustrated by way of example in FIG. 1, for instance, the radio access network 16 may include a base transceiver station (BTS) 30, which communicates with wireless communication device over an air interface 32, and a base station controller (BSC) 34, which controls BTS 30 and thus controls various aspects of communication over the air interface. As further shown, the BSC 34 of the radio access network may then be connected with a gateway such as a packet data serving node (PDSN) 36, which provides packet-switched connectivity with transport network 18.

In practice, the wireless communication device may acquire wireless packet data connectivity through any applicable wireless communication protocol, in order to then engage in wireless packet data communications with network server 20. By way of example, under the well known CDMA2000 protocol, the wireless communication device 14 may send an origination request message over an air interface access channel to the radio access network 16. In response, after the radio access network 16 authenticates the wireless communication device 14, the BSC 34 may direct the BTS 30 to assign an air interface traffic channel over which the wireless communication device can engage in bearer communication. Further, the BSC 34 may signal to the PDSN 36, and the PDSN 36 may negotiate with the wireless communication device 14 to establish a data link layer connection over which packet data can be communicated. And the PDSN 36 and/or a mobile-IP home agent (not shown) will then assign an IP address to the wireless communication device 14, which the wireless communication device can then use to engage in packet-data communication on network 18.

In a preferred embodiment, the wireless communication device 14 will subscribe to service with the wireless service provider, and the wireless service provider will charge a price for providing the wireless communication device with wireless communication service. Accordingly, the wireless service provider may maintain account/billing system 22, which may define the account for the wireless communication device 14 and may thus include a record of how much the account holder will be charged for using the wireless communication device to engaging in wireless communication, or for the right to engage in such wireless communication.

As such, the account/billing system 22 may include an account record for the wireless communication device, and the account/billing system 22 may regularly bill the account holder, requesting the account holder to pay the price. For instance, the account/billing system 22 may generate and send to the account holder a monthly invoice requiring the account holder to pay the price. The price may be a recurring charge and/or may be defined according to any of a variety of pricing schedules. Further, the price may relate to communication in which the wireless communication device engages in according to the present invention (such as to report health status information) and/or to other wireless communication in which the wireless communication device engages. For instance, the price may be a price for the wireless communication device to engage in basic telephone service, notwithstanding the fact that the device might report health status information through data communication that is distinct from the telephone service.

Network server 20, in turn, may comprise any programmed computer or similar node with which wireless communication device 14 can communicate via radio access network 16. Network server 20 could be owned and operated by the wireless service provider or by another party, such as a health-service provider for instance. In accordance with the exemplary embodiment, network server 20 will receive from the wireless communication device 14 an indication of at least one health characteristic of the person, and the network server will grant a discount on the price that the wireless service provider charges for providing wireless communication service to the wireless communication device.

In practice, as noted above, the server 20 may trigger a grant of price discount by simply comparing the reported health characteristic(s) with a predefined threshold (one or more thresholds), to determine if the at least one reported health characteristic meets the threshold. If the server thereby determines that the at least one reported health characteristic meets the threshold, then the server may trigger a grant of price discount. Otherwise, the server may decline to trigger a grant of price discount.

Further, the server 20 may receive multiple health characteristic reports from the wireless communication device 14, all at once or at separate times, and regarding one or more types of health characteristics, the server 20 may store the received health characteristic data, combine the data together in some manner (such as by averaging or totaling it for instance) to obtain a combined measure, and then determine whether the combined measure meets a defined threshold. If so, the server may then trigger the price discount. For instance, if the server 20 receives from the wireless communication device 14 periodic reports of the number of steps taken by the person, as determined by a pedometer for instance, the server 20 could maintain a running average of the reported number of steps per day and could trigger a price reduction if the average stays above a certain level for a designated period of time, indicating that the person is walking sufficiently.

Once the server 20 triggers a grant of price discount, the server 20 will then preferably register the price discount, through communication with the wireless service provider's account/billing system 22. To do so, the server 20 may send a signal to a designated entity (e.g., another server) in the account/billing system 22, directing the account/billing system 22 to apply the discount to the service account of the wireless communication device 14. Account/billing system 22 may then responsively apply that discount, such as by reducing the price set forth in the account record of the wireless communication device 14. Thus, when the account/billing system 22 next bills the account holder for providing wireless communication service to the wireless communication device, the bill would indicate the reduced price. Alternatively, the account/billing system 22 may apply the discount by issuing a credit to the account holder, and the credit could similarly be presented on the next bill sent to the account holder.

As illustrated in FIG. 1 by the dashed box 30 surrounding the network server 20 and the account/billing system 22, it is possible that the network server 20 and account/billing system 22 could be integrated together. For instance, the network server 20 could be a component of the account/billing system 22, or a single server could be provided to carry out both the function of the network server 20 and the function of the account/billing system 22. If the two elements are combined together, the act of sending a signal from the network server 20 to the account/billing system 22 could involve sending the signal over an internal system bus or other connection mechanism. Further, the functions could just as well be integrated together and controlled by a single processor, in which case there may be no need to communicate any signals from the server to the account/billing system.

Figure 2:
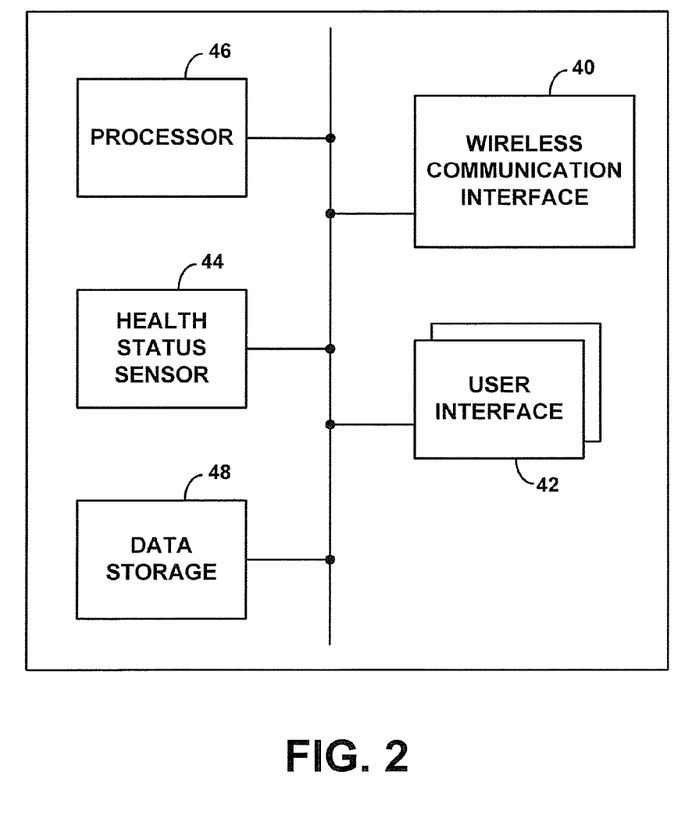
FIG. 2 is a simplified block diagram of a wireless communication device arranged to operate in accordance with the exemplary embodiment.

Referring next to FIG. 2, a simplified block diagram of an exemplary wireless communication device with integrated health status sensor is provided. As shown, the device includes a wireless communication interface 40, a user interface 42, a health status sensor 44, a processor 46, and data storage 48, all of which may be coupled together by a system bus or other mechanism 50.

Wireless communication interface 40 functions to communicate over air interface 32 with the radio access network 16. As such, wireless communication interface 40 may comprise an "MSM" chipset of the type manufactured by Qualcomm Incorporated, for instance, as well as an internal or external antenna. User interface 42 may comprise input/output components, such as a keypad for data entry and a display screen for data output. Health status sensor 44 may then take the form of any of the health status sensors noted above, or any other health status sensor now known or later developed, and may work together with an internal or external sensor element (not shown) for applying to the person.

Processor 46 may comprise one or more general purpose processors (e.g., INTEL microprocessors) and/or one or more special-purpose processors (e.g., digital signal processors). And data storage 48 may comprise one or more volatile and/or non-volatile storage components, such as magnetic, optical, organic, or other storage mechanisms, and may be integrated in whole or in part with processor 46. Data storage 48 functions, at least in part, to hold health characteristic information determined by health status sensor 44. Further, data storage 48 contains program instructions executable by processor 46 to carry out various functions described herein.

Figure 3:
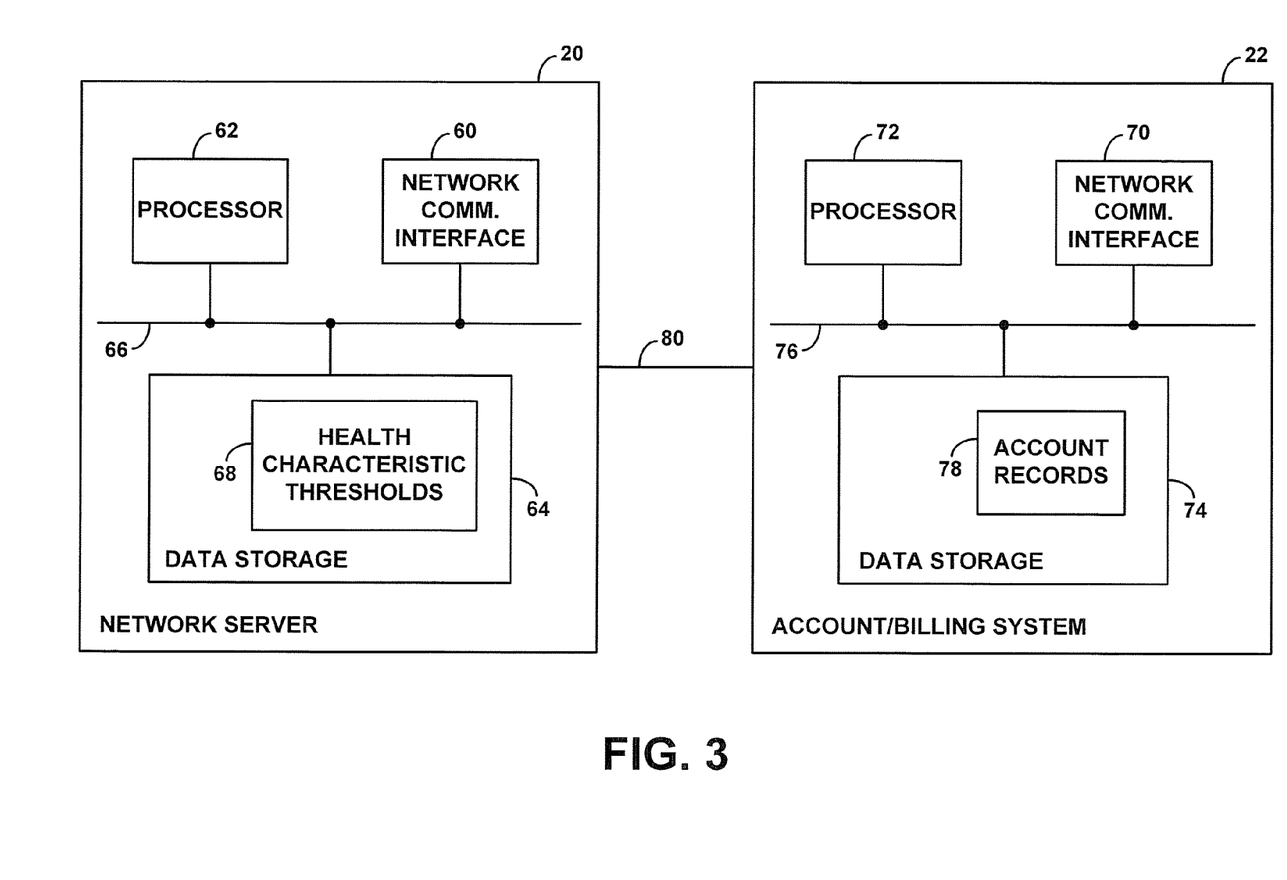
FIG. 3 is a simplified block diagram of network server and wireless service provider account/billing system, arranged to operate in accordance with the exemplary embodiment.

FIG. 3 next provides a simplified block diagram of a combination of network server 20 and account/billing system 22. As shown, the network server 20 includes a network communication interface 60, a processor 62, and data storage 64, coupled together by a system bus or other mechanism 66. And account/billing system 22 includes a network communication interface 70, a processor 72, and data storage 74, coupled together by a system bus or other mechanism 76.

Each network communication interface 60, 70 functions to facilitate communication on network 18 or other sort of communication, including possibly wired and/or wireless communication with each other and/or with other entities. Each network communication interface may, for instance, comprise an Ethernet network interface card or other mechanism. Further, each processor 62, 72 may comprise one or more general purpose processors and/or one or more special-purpose processors. And each data storage 64, 74 may comprise one or more storage components.

In the exemplary embodiment, the data storage 64 of network server 20 contains threshold data 68 indicating one or more health characteristic thresholds usable to trigger a grant of discount on wireless communication service. Such thresholds could be defined on a per subscriber basis, possibly to serve individual health goals. (Further, the threshold data could alternatively be stored in data storage 74 of account/billing system 22 and referenced by network server 20 or by account/billing system 22.) Data storage 64 further contains program instructions executable by processor 62 to carry out various functions described herein.

As shown, data storage 74 of account/billing system contains account data 78, including an account record for wireless communication device 14, which, as noted above, would indicate a price that the wireless service provider charges for providing wireless communication service for the wireless communication device. Further, data storage 74 contains program instructions executable by the processor 74 to carry out various functions described herein, such as registering a wireless service price discount.

FIG. 3 depicts a link 80 extending between network server 20 and account/billing system 22. This link could be a wired and/or wireless link and could comprise network 18 itself. The link enables the network server 20 to interact with account/billing system 22, such as to instruct the account/billing system 22 to register a wireless service price discount in response to reported health characteristic data meeting a threshold.

3. Example Operation

Figure 4:
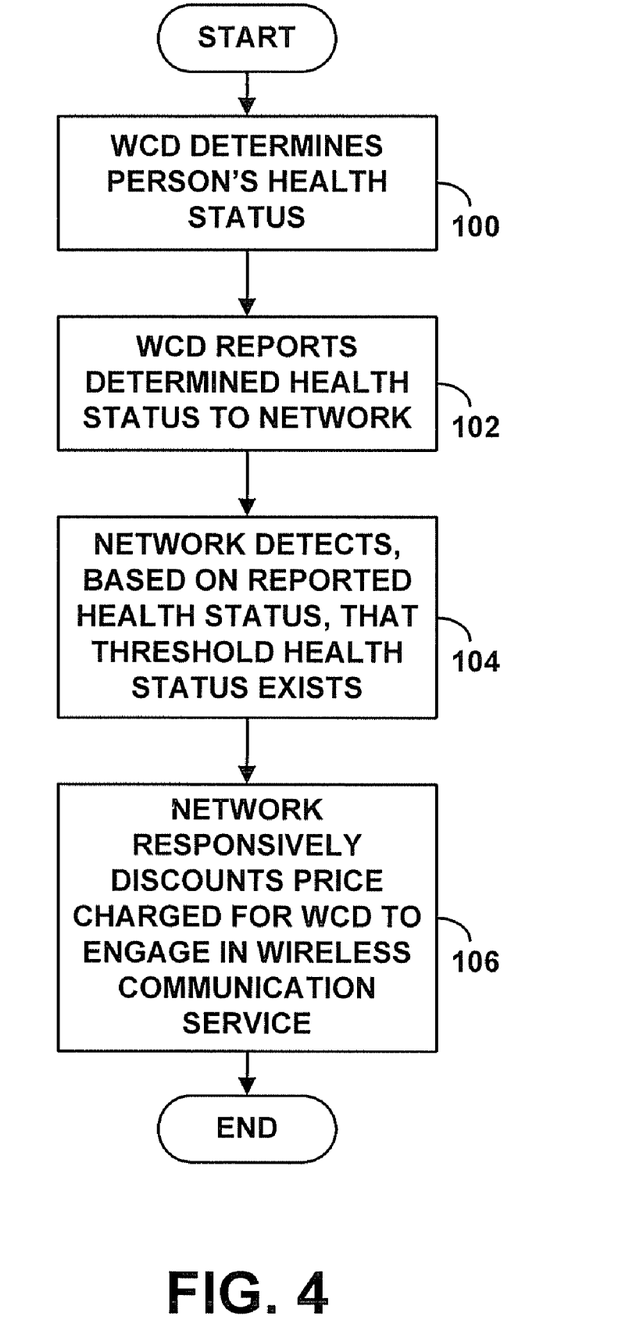
FIG. 4 is a flow chart depicting functions that can be carried out in accordance with the exemplary embodiment.

Finally, FIG. 4 is a flow chart depicting in summary a set of functions that can be carried out in accordance with the exemplary embodiment. As shown in FIG. 4, at step 100, a wireless communication device determines a person's health characteristic, such as by receiving an indication of the health characteristic from a health status sensor applied to the person. At step 102, the wireless communication device then transmits an indication of the determined health characteristic via a radio access network to a network server. At step 104, the network server then determines, based on the reported health characteristic, that a threshold health status exists. And at step 106, the network server then responsively registers a discount on a price that a wireless service provider charges for providing the wireless communication device with wireless communication service.

4. Conclusion

An exemplary embodiment of the invention has been described above. Those skilled in the art will appreciate that variations from the embodiment described are possible, while remaining within the scope of the invention, which is defined by the claims.

What is claimed is:

1. A method comprising:
   receiving into a network server a message transmitted to the network server from a wireless communication device carried by a person, wherein the message transmitted from the wireless communication device contains data indicating at least one health characteristic of the person, and wherein a wireless service provider charges a price for providing wireless communication service for the wireless communication device; and
   based on the at least one reported health characteristic, granting a discount on the price that the wireless service provider charges for providing wireless communication service for the wireless communication device.

2. The method of claim 1, further comprising:
   determining that the at least one reported health characteristic meets a threshold,
   wherein granting the discount based on the at least one reported health characteristic comprises granting the discount in response to determining that the at least one reported health characteristic meets the threshold.

3. The method of claim 2, wherein determining that the at least one reported health characteristic meets the threshold comprises receiving multiple health characteristic reports transmitted from the wireless communication device, establishing a measure based on the multiple health characteristic reports, and determining that the measure meets the threshold.

4. The method of claim 1, wherein granting the discount on the price comprises reducing the price.

5. The method of claim 1, wherein granting the discount on the price comprises applying a credit to a service account for the wireless communication device, to thereby effectively reduce the price.

6. The method of claim 1, wherein the at least one health characteristic of the person comprises a quantity of exercise in which the person has engaged.

7. The method of claim 6, wherein the quantity of exercise comprises a count of steps determined to have been taken by the person.

8. The method of claim 7, wherein the wireless communication device contains a pedometer and, when the wireless communication device is carried by the person while the person is in motion, the pedometer determines the count of steps taken by the person.

9. The method of claim 7, wherein the count of steps is determined by the wireless communication device by receiving the count reported from a pedometer carried by the person while the person is in motion.

10. The method of claim 1, wherein the at least one health characteristic of the person comprises a health characteristic established by a body sensor applied to the person and reported from the body sensor to the wireless communication device.

11. The method of claim 10, wherein the body sensor comprises a sensor selected from the group consisting of a cholesterol sensor, a heart rate sensor, a blood sugar sensor, a blood pressure sensor, and a body temperature sensor.

12. The method of claim 1, wherein the wireless communication device comprises a cellular telephone.

13. A system comprising:
- a portable wireless communication device usable by a person to engage in wireless communication service via a radio access network, wherein a wireless service provider charges a price for providing wireless communication service for the portable wireless communication device; and
- a network server communicatively accessible by the portable wireless communication device via the radio access network,
- wherein the portable wireless communication device includes device logic executable by a processor to report at least one health characteristic of the person via the radio access network to the network server, and
- wherein the network server includes server logic executable by a processor, based on the at least one reported health characteristic, to grant a discount on the price that the wireless service provider charges for providing wireless communication service for the portable wireless communication device.

14. The system of claim 13, wherein the server logic is executable to determine that the at least one reported health characteristic meets a threshold, and wherein the server logic grants the discount on the price in response to determining that the at least one reported health characteristic meets the threshold.

15. The system of claim 13, wherein the server logic is executable to receive multiple reported health characteristics from the portable wireless communication device, to establish a measure based on the multiple reported health characteristics, to determine that the measure meets the threshold, and to grant the discount in response to determining that the measure meets the threshold.

16. The system of claim 13, wherein the server logic is executable to grant the discount on the price at least in part by causing a signal to be sent to the wireless service provider directing the wireless service provider to apply a price discount to a service account of the wireless communication device.

17. The system of claim 13, wherein the portable wireless communication device comprises a cellular telephone.

18. The system of claim 13, wherein the health characteristic comprises a count of steps taken by the person.

19. The system of claim 18, wherein the portable wireless communication device includes a pedometer that establishes the count of steps.

20. The system of claim 18, further comprising a body sensor applicable to the person, wherein the body sensor measures the health characteristic of the person, and wherein the device logic receives an indication of the measured health characteristic from the body sensor.

21. The system of claim 20, wherein the body sensor is integrated in the portable wireless communication device.

22. The system of claim 20, wherein the body sensor communicates with the portable wireless communication device via a personal area network.

* * * * *